United States Patent [19]

Woods et al.

[11] Patent Number: 5,019,629
[45] Date of Patent: May 28, 1991

[54] POLYMERIZABLE STYRYLOXY RESINS AND COMPOSITIONS THEREOF

[75] Inventors: John Woods, Dublin, Ireland; John Rooney, Basking Ridge, N.J.; Pauline Coakley, Dublin, Ireland

[73] Assignee: Loctite Corporation, Newington, Conn.

[21] Appl. No.: 432,934

[22] Filed: Nov. 6, 1989

[30] Foreign Application Priority Data

Nov. 10, 1988 [IE] Ireland ................... 3380/88

[51] Int. Cl.$^5$ ........................... C08F 261/06
[52] U.S. Cl. .................... 525/312; 526/301; 526/312; 526/313; 528/49; 528/110
[58] Field of Search .............. 525/312; 526/301, 312, 526/313; 528/49, 110

[56] References Cited

U.S. PATENT DOCUMENTS

| | | | |
|---|---|---|---|
| 3,327,019 | 6/1967 | Mylenbusch et al. | 260/861 |
| 4,486,582 | 12/1984 | Hefner, Jr. | 526/301 |
| 4,543,397 | 9/1985 | Woods et al. | 525/455 |
| 4,732,956 | 3/1988 | Woods et al. | 526/260 |

FOREIGN PATENT DOCUMENTS 1448516 9/1976 United Kingdom .

OTHER PUBLICATIONS

Chemical Abstracts, vol. 63, Rutherford J. Gettens, 9968 c-d (Oct. 11, 1965).

*Primary Examiner*—Bernard Lipman
*Attorney, Agent, or Firm*—Vidas & Arrett

[57] ABSTRACT

Cationically polymerizable styryloxy resins having urethane linkages, represented by the formula III

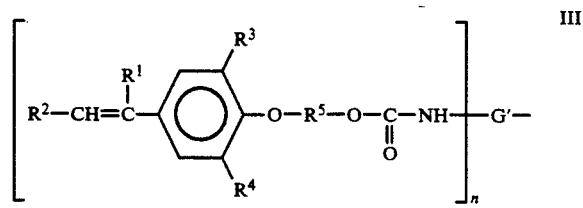

wherein
$R^1$ and $R^2$ are H, or one of $R^1$ and $R^2$ is H and the other is methyl;
$R^3$ and $R^4$ (which may be the same or different) are H, lower alkyl, or alkoxy if $R^2$ is not methyl;
$R^5$ is a divalent hydrocarbon radical;
$G^1$ is an n-valent hydrocarbon radical free of amino, aliphatic thiol, aliphatic hydroxyl or other groups which interfere with cationic polymerization;
and n is an integer of 2 or more.

$G^1$ is a hydrocarbon backbone which is not interrupted by a hetero atom. Preferably $G^1$ is a residue of a diene homopolymer or copolymer, in which case the resins produce flexible polymers. The resins are polymerized with a cationic polymerization initiator or latent acid catalyst. The resins have utility in the field of electronics.

9 Claims, No Drawings

POLYMERIZABLE STYRYLOXY RESINS AND COMPOSITIONS THEREOF

BACKGROUND OF THE INVENTION

1. Field of the Invention

This invention relates to cationically polymerisable styryloxy resins and compositions containing such resins together with a polymerisation initiator.

2. Description of the Related Art

In U.S. Pat. No. 4,543,397 Woods et al, assigned to Loctite (Ireland) Limited there are described polyfunctional cationically polymerisable styryloxy compounds of the formula I or II

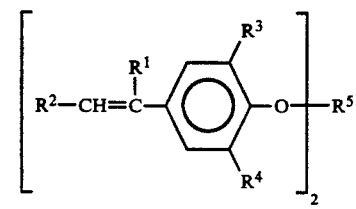

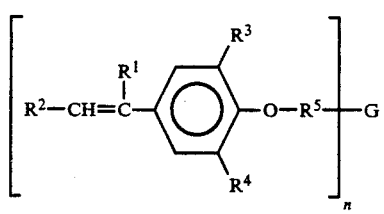

where $R^1$ and $R^2$ are H, or one of $R^1$ and $R^2$ are H and the other is methyl; $R^3$ and $R^4$ are H, lower alkyl, or alkoxy if $R^2$ is not methyl; $R^5$ is a divalent hydrocarbon radical; G is a multivalent organic or inorganic radical free of amino, aliphatic hydroxyl, aliphatic thiol or other groups which interfere with cationic polymerisation; and n is an integer of two or more.

Example 2 thereof describes the preparation of an adduct of vinyl guaiacol and allyl glycidyl ether, followed by reaction of this adduct with a polyfunctional isocyanate resin commercially available under the Trade Mark BAYER Desmodur L-75 to form a high molecular weight resin. However due to the polyfunctional nature of Desmodur L-75, this resin would have urethane groupings in the backbone G.

U.S. Pat. No. 4,486,582 Hefner describes reaction monomers prepared by reacting (1) an aromatic compound containing a polymerisable ethylenically unsaturated group and a group containing a hydrogen atom reactive with an NCO group (2) a compound having at least one oxyalkylene group and at least one group containing at least one hydrogen atom reactive with an NCO group, and (3) a compound having an average of more than one NCO group per molecule.

However because of the oxyalkylene groups, Hefner's monomers would produce resins which would be susceptible to hydrolytic breakdown.

British Patent Specification No. 1,448,516 Kao Soap Co. Ltd. describes vinyl-terminated prepolymers formed by reacting (a) an organic polyisocyanate compound with (b) at least one equivalent of a compound having the formula

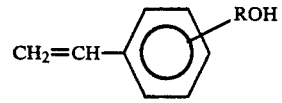

wherein R is a group —$CH_2$— or

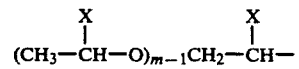

in which m is an integer from 1 to 4 and X is —H or —$CH_3$. However such prepolymers are not styryloxy compounds and have limited capacity for cationic polymerisation.

SUMMARY OF THE INVENTION

The present invention is directed to a new group of cationically polymerisable styryloxy resins having urethane linkages, represented by the formula III

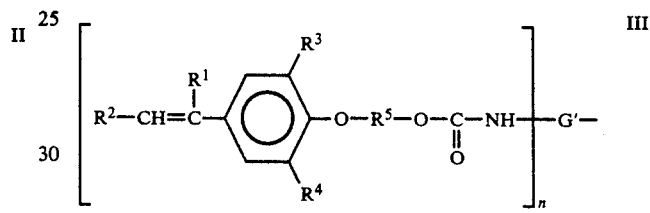

wherein $R^1$ and $R^2$ are H, or one of $R^1$ and $R^2$ is H and the other is methyl;

$R^3$ and $R^4$ (which may be the same or different) are H, lower alkyl, or alkoxy if $R^2$ is not methyl;

$R^5$ is a divalent hydrocarbon radical; $G^1$ is the residue of an n-valent isocyanate prepolymer prepared by reaction of hydroxyl terminated hydrocarbon polymer halohydrocarbon selected from the groups consisting of a diene homopolymers and copolymers with an aromatic or aliphatic diisocyanate, said prepolymer being free of amino, aliphatic thiol, aliphatic hydroxyl or other groups which interfere with cationic polymerisation;

and n is an integer of 2 or more.

$G^1$ may suitably be an aromatic, aliphatic or cycloaliphatic hydrocarbon radical, which may be saturated or unsaturated, substituted or unsubstituted, provided that the hydrocarbon chain and/or ring is not interrupted by a hetero atom. In one preferred embodiment, which provides particularly advantageous flexible resins, $G^1$ comprises an unsaturated aliphatic hydrocarbon radical, more particularly a residue of a diene homopolymer or copolymer, which may have a number average molecular weight in the range from about 400 to about 25,000, more particularly 1,000 to 5,000.

The invention also provides a polymerisable composition comprising a resin of formula III as defined above and a cationic polymerisation initiator or latent acid catalyst.

The resins of formula III are suitably derived from (a) a styrene compound of the formula IV

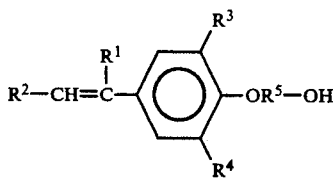

wherein $R^1$-$R^5$ are as defined above; and (b) a compound having a hydrocarbon chain and/or ring, and —NCO terminal groups.

The compound (b) may be derived from:

(b¹) a compound having a hydrocarbon chain and/or ring, and terminal groups containing a hydrogen atom reactive with an NCO group, and (c) a polyisocyanato compound.

The compound (b¹) may suitably be one of the hydroxyl-terminated diene polymers or copolymers described in U.S. Pat. No. 3,674,743 Verdol et al. The diene employed to make the polymer may have up to 12 carbon atoms preferably up to 6 carbon atoms, and may be substituted with one or more lower alkyl, aryl or halogen groups. Suitable dienes include buta-1,3-diene, 2-methyl-buta-1,3-diene (isoprene), 2-chlorobuta-1,3-diene (chloroprene), and 2,3-dimethyl-buta-1,3-diene. Buta-1,2-diene may also be used. Copolymers of any of these monomers with a compatible comonomer such as styrene may also be used.

The compound (c) may suitably be an aliphatic or aromatic diisocyanate such as 2,4-toluene diisocyanate or any of the other diisocyanates mentioned in U.S. Pat. No. 3,674,743 Verdol et al at column 5 lines 7-20.

The compound (a) may suitably be prepared by methods described in U.S. Pat. No. 4,543,397 Woods et al, particularly at column 2 lines 34-65.

In the formulae III and IV above, it is generally preferred that $R^3$ is H, methyl or methoxy, and $R^4$ is H. However, other lower alkyl or alkoxy groups may be included as substituents $R^3$ and/or $R^4$. The term "lower" as used in this Specification means having up to about 5 carbon atoms.

$R^5$ is preferably a saturated or unsaturated linear hydrocarbon, most suitably having up to about 5 carbon atoms; or a cycloaliphataic or aromatic hydrocarbon having up to about 10 carbon atoms. Examples of $R^5$ groups are methylene, ethylene, propenylene, butylene or 1,4-dimethylenebenzene.

The only limitation on substitution of $G^1$ is that is must not interfere with cationic polymerization of the styryloxy groups. $G^1$ must not include any strongly electron-withdrawing group in conjugation with the styryloxy group oxygen atom as such groups will interfere with vinyl cationic polymerizations. Amines, aliphatic hydroxyls, and aliphatic thiols are known to prevent or slow vinyl cationic polymerizations ["Developments in Polymerization-1" R. N. Howard ed., Applied Science Publishers, 1979, pg 80]. Inclusion of these groups in $G^1$ should therefore also be avoided.

Polymerization of the inventive monomers may be accomplished by conventional acid and Lewis acid cationic initiators such as methane sulfonic acid, toluene sulfonic acid and boron trifluoride etherate. UV cationic initiators may also be used. Such UV cationic photoinitiators include salts of a complex halogenide having the formula: $[A]_b$-$[MX_3]^{(e-f)}$ where A is a cation selected from the group consisting of iodonium, sulfonium, pyrylium, thiopyrylium and diazonium cations, M is a metalloid, and X is a halogen radical, b equals e minus f, f equals the valence of M and is an integer equal to from 2 to 7 inclusive, e is greater than f and is an integer having a value up to 8. Examples include di-p-tolyl iodonium hexafluorophosphate, diphenyl iodonium hexafluorophosphate, diphenyl iodonium hexafluoroarsenate and GE 1014 (trademark of General Electric Company), a commercially available sulfonium salt of a complex halogenide.

The styryloxy resins of the present invention have a hydrocarbon backbone and therefore produce crosslinked polymers which have better hydrolytic stability and resistance to chemical attack than comparable polymers which have oxyalkylene or ester linkages in the backbone. The inventive resins have particular utility in the field of electronics (for example as potting compositions), where the hydrophobicity of the polymers produced from the resins enables insulating properties to be retained even in the presence of moisture. The resins according to the invention having a diene polymer backbone have the added advantage that they produce flexible polymers which exhibit advantageous behaviour at low temperatures and which have good resistance to thermal shock These properties are also important for electronic applications.

DESCRIPTION OF THE PREFERRED EMBODIMENTS

The invention may be illustrated by reference to the following non-limiting Examples.

EXAMPLE 1

A 5-liter glass reactor equipped with a reflux condenser, mechanical stirrer and powder inlet port, was charged with 366 g of 4-hydroxybenzaldehyde, 528 g of ethylene carbonate and 1.5 L of methylisobutyl ketone (MIBK). The mixture was stirred. On solution of aldehyde and carbonate 414 g of anhydrous potassium carbonate was slowly added. The stirred mixture was refluxed for four hours after which time t.l.c. analysis indicated complete consumption of the phenolic starting compound. The reaction mixture was cooled and 1.5 L of 3M sodium hydroxide solution added. The organic layer was separated, washed with $H_2O$ and dried over anhydrous sodium sulfate. The dried solution was filtered and the solvent removed under reduced pressure to give 496 g of an orange coloured oil. Gel permeation chromatographic analysis (G.P.C.; 10$\mu$ styrogel columns, $10^3$, 500 and 100 Angstrom, $CH_2Cl_2$ eluent; R.I. detector) showed the oil to consist mainly of 2 components with elution volumes of 24.9 mls (Approx. 80%) and 23.7 mls (Approx. 20%) along with minor quantities of higher molecular weight products. Vacuum distillation of the crude product gave 330 g. (66%) of 4-(2'-hydroxy-ethoxy) benzaldehyde (formula V) (170°-190° C. at 0.4 mbar) which was shown by G.P.C. to also contain approx. 5% of a higher molecular weight product. The infra-red (NaCl disc) spectrum of the distilled product showed peaks at 3,580 cm$^{-1}$ (—OH group); 1675, 2920 cm$^{-1}$ (AR—CHO group); 1590 cm$^{-1}$ (AR—H group) and 1255 cm$^{-1}$ (AR—O—C—group) which confirms the structural assignment.

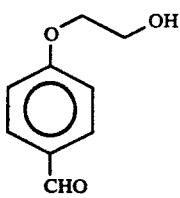 V

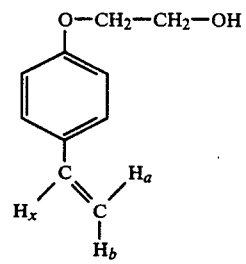 VII

EXAMPLE 2

A 5 liter glass reactor, equipped with a reflux condenser, $N_2$ purge, powder inlet port, dropping funnel and mechanical stirrer was charged with dry tetrahydrofuran (1.5 L) and sodium amide (91 g of 90%, 2.1 m). To the stirred suspension was added methyltriphenylphosphonium bromide (750 g, 2.1 m), and the mixture stirred at room temperature for 3 hours. A solution of 290.5 g of 4-(2'-hydroxyethoxy) benzaldehyde (prepared as described in Example 1) in 200 mls of dry tetrahydrofuran was added dropwise over 1.5 hours. The stirred mixture was refluxed for 3 hours after which time t.l.c. analysis indicated complete consumption of the starting aldehyde. The mixture was cooled and $H_2O$ (4 L) was added. The mixture was extracted with dichloromethane (4×500 mls) and the combined extracts dried over anhydrous $Na_2SO_4$. The desiccant was removed by filtration and the solvent distilled under reduced pressure to yield 850 g of a viscous semi-solid residue. The residue was extracted with petroleum spirit b.p. 40°-60° C. (5×500 mls) followed by an 80/20 blend of petroleum spirit and diethyl ether, until GPC and t.l.c. analysis indicated the residue to comprise only of triphenylphosphine oxide. The extracts were combined and the solvent reduced by vacuum distillation to approximately one liter. The triphenyl phosphine oxide which had precipitated was removed by filtration and the remainder of the solvent in the filtrate was removed under reduced pressure to yield an oil (413 g). The oil was distilled under vacuum to yield 4-(2'-hydroxyethoxy) styrene (114.4 g, 40%, 140°-160° C. at 0.8 mbar) as a colourless oil which solidified on cooling. G.P.C. analysis indicated only one component (i.e. 100% purity) and the structure of the product of formula VII:.

was confirmed by spectroscopic analysis. $^1HNMR(CDCl_3, 60MHz) \tau$ 2.90, m, 4H, AR—H, $\tau$ 3.35, m, 1H, AR—CH=C; $\tau$ 4.4, q, 1H, AR—C=C—$H_a$, (Jax=18Hz, Jab=2Hz); $\tau$ 4.86, q, 1H, AR—C=C—$H_b$, (Jbx=11Hz, Jba=2Hz); $\tau$ 5.99, m, 4H, —OCH$_2$CH$_2$—O—; $\tau$ 7.3, 1H broad S, —OH. I.R. (NaCl); 3540 $cm^{-1}$ —OH group, 1620 $cm^{-1}$ AR—CH=CH$_2$; 1590 $cm^{-1}$, AR—H; 1245 $cm^{-1}$ AR—O—C—.

EXAMPLE 3

A 1-L glass reactor equipped with a sealed mechanical stirrer, $N_2$ purge, dropping funnel and vacuum pump connection was charged with hydroxyl terminated poly(butadiene) (60.25 g, $\overline{M}n$=2,800, 0.02 m,) supplied by Arco Chemical Co. under trade name Poly BD R-45HT. The gas purge was disconnected and the reactor evacuated to 0.9 mbar pressure. The contents were stirred, heated to 110° C. for 2 hours and allowed to cool. The $N_2$ feed was opened and the vacuum pump disconnected. Benzoyl chloride (0.018 g) was added and the mixture stirred for 5 minutes. Toluene diisocyanate (8.3 g, 0.048 m) was added dropwise over 5 minutes and the mixture stirred for 3.5 hours. The GPC chromatogram (10$\mu$ styragel columns, $10^3$, 500 and 100 Angstrom, $CH_2Cl_2$ eluent, UV detector $\lambda$=250 nm) showed a single broad peak with elution volume=18.0 ml and a much smaller peak with elution volume=25.5 ml corresponding to TDI (approx. 2% of total). Since the starting polyol has no UV absorption at 250 mm, the major product corresponds to the diisocyanate prepolymer of poly(butadiene). An I.R. spectrum of the product showed the characteristic isocyanate group peak at 2,240 $cm^{-1}$. 4-(2'-hydroxyethoxy) styrene (7.22 g, 0.44 m) (prepared as described in Example 2) and 1,4 benzoquinone (0.2 g), were added to the stirred mixture and heated at 60° C. for 46 hours. The I.R. spectrum indicated that all of the isocyanate prepolymer had been consumed as the peak at 2,240 $cm^{-1}$ had disappeared. GPC analysis showed a main broad peak with elution volume=16.5 ml corresponding to the styryloxy terminated urethane of structure VIII:

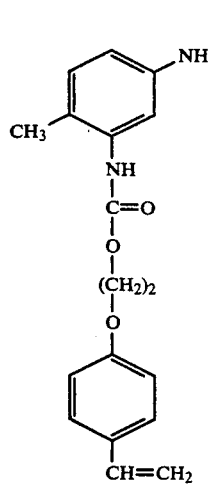 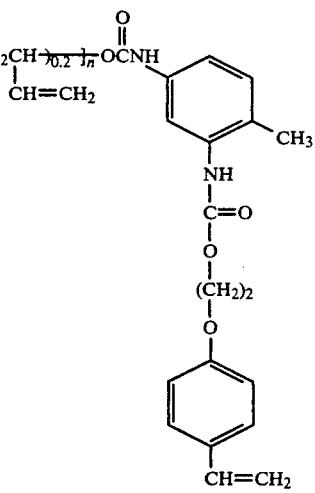

VIII wherein n is approximately 52, corresponding to approximately 42 (—CH$_2$CH=CHCH$_2$—) groups and 10

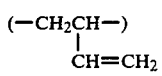

groups, randomly distributed.

EXAMPLE 4

Methane sulfonic acid (one drop) was added to the styryloxy resin of Example 3 (1 g). A light purple coloured gel was immediately formed which was found to be insoluble in dichloromethane (CH$_2$Cl$_2$).

EXAMPLE 5

Styryloxy resin of Example 3 (1 g) was dissolved in CH$_2$Cl$_2$ (5 mls). One drop of methanesulfonic acid was added to the solution. A polymerized gel immediately precipitated. A similar experiment was carried out using poly (butadiene) resin instead of styryloxy resin. No gel formed on addition of the acid.

EXAMPLE 6

Photocationic catalyst GE 1014 (0.03 g. supplied by General Electric Company) was blended with styryloxy resin of Example 3 (1.00 g) and a drop of the blended composition exposed to ultra-violet light (UV) from a medium pressure mercury arc lamp (UVA LOC 1000 Lamp supplied by Loctite Deutschland GmbH) operating at 40 W/cm. The liquid composition was located 20 cms directly below the arc. After 60 seconds irradiation, the composition had cured tack free. A similar experiment was carried out in which the catalyst was omitted. After irradiation, the resin had skin-cured only and the surface was tacky.

EXAMPLE 7

To a solution of 122 g 4-hydroxybenzaldehyde in 500 ml acetone was added 276 g potassium carbonate. This mixture was stirred for 15 minutes. A solution of 133 g allyl bromide in 200 mls acetone was then added dropwise over 30 minutes. The resulting mixture was heated at reflux for 1 hour, left standing for a further 16 hours and finally heated at reflux for 2 hours. After filtration, the solvent was removed by distillation leaving 175 g of a reddish liquid. This residue was distilled under reduced pressure (B.Pt. 104°–114° C. at 1.5 mm Hg) to yield 130 g of a pale yellow liquid which was identified by infrared and n.m.r. spectroscopy as 4-allyloxybenzaldehyde.

To a solution of 9.36 g potassium metal in 500 ml tert-butanol was added 85.68 g methyltriphenylphosphonium bromide. The resulting yellow suspension was stirred for 20 minutes and 32.4 g 4-allyloxybenzaldehyde was then added over 10 minutes. This mixture was stirred for 30 minutes and then allowed to stand overnight. After filtration the solvent was removed under reduced pressure leaving 107 g of red semi-solid residue. Petroleum ether (B.Pt. 40°–60° C.) was added to the residue precipitating a solid which was filtered. After removal of the petroleum ether, the remaining resin was distilled under reduced pressure (B.Pt 68°–82° C. at 0.4 mm Hg) yielding 26.7 g of a clear colourless liquid which was identified by infrared and n.m.r. spectroscopy as 4-allyloxystyrene (Proton NMR: (CDCl$_3$) $\tau$=4.50, 4.58, doublet, allyloxymethylene protons; $\tau$=5.0–6.5, multiplets, allyl and vinyl group protons; $\tau$=6.80, 6.95, 7.30 and 7.45, quartet, aromatic protons).

EXAMPLE 8

A light sensitive composition was prepared by blending together the following ingredients:

| | |
|---|---|
| styryloxy resin of Example 3 | 3.5 g |
| 4-allyloxystyrene of Example 7 | 1.5 g |
| photocationic catalyst GE 1014 | 0.2 g |

The liquid composition was poured into a cylindrical mould 1 mm deep and 8 mm diameter and exposed to UV light from a SUPERLITE 201 (supplied by Lumatec GmbH), through a one meter fluid filled light-guide. The composition was located 1 cm directly below the tip of the light-guide. After 10 minutes irradiation, the composition was fully cured and had a tack-free surface.

EXAMPLE 9

A similar experiment to that described in Example 8 was carried out, in which the cationic catalyst was replaced with 0.1 g of the free radical photoinitiator, 2,2-dimethoxy-2-phenylacetophenone (IRGACURE 651, Ciba Geigy). After the 10 minutes irradiation period, the composition had cured but the surface was tacky.

EXAMPLE 10

A solution of 21.2 g of benzoin and 430 g toluene was prepared by heating the mixture to 70° C. 19.5 g of p-toluenesulfonyl chloride was then added and the mixture cooled to 30° C. 6.33 g of powdered sodium hydroxide was then added and the mixture stirred for 2.5 hours. After a further 16 hours the mixture was washed with 3×150 ml portions of water and the organic fraction dried over sodium sulfate. The dessicant was removed by filtration and the toluene solution concentrated by removal of part of the solvent under reduced pressure. The mixture was cooled to −18° C. After 16 hours 9.53 g of a crystalline precipitate had formed which was removed by filtration and dried. This material was found to be unreacted benzoin. The filtrate was further concentrated and again cooled to −18° C. After 1 hour a second lot of crystals had formed. The crystals were collected by filtration and dried to give 7.64 g of crude product. This was recrystallized from industrial methylated spirit to yield 4.64 g of pure α-tosyloxy-α-phenylacetophenone, the structure (formula IX) was confirmed by NMR and IR spectroscopy and by gel permeation chromatography (GPC):

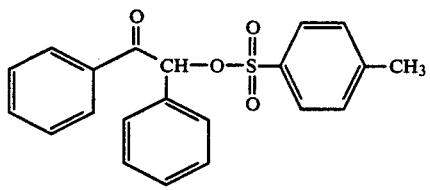

IX

60MH$_z$, Proton NMR (CDCl$_3$): $\tau$=2.2–3.0, multiplet, 14H, aromatic protons; $\tau$=3.4, singlet, 1H, methine proton; $\tau$=7.75, singlet 3H, methyl group.

I.R. (film cast on KBr disc from CDCl$_3$): 3020 cm$^{-1}$, (W), AR—H; 1690 cm$^{-1}$, (S), aromatic carbonyl group, 1590 cm$^{-1}$, (m), AR—H; 1320 and 1140 cm$^{-1}$, (S), —SO$_2$—O— group.

GPC analysis (microstyrogel columns) indicated only one component, higher in molecular weight than either starting material.

EXAMPLE 11

A similar experiment to that described in Example 8 was carried out in which the cationic catalyst GE 1014 was replaced with 0.1 g of α-tosyloxy-α-phenylacetophenone (prepared as described in Example 10). After the irradiation period, the composition had cured but the surface was tacky.

EXAMPLE 12

A thin film, 75μ thick, of the composition of Example 8 was prepared on a 4×1 inch glass microscope slide. The film was exposed to UV light from a medium pressure mercury arc lamp (UVA LOC 1000) operating at 80W/cm. The coated substrate was located 20 cm directly below the arc. After 10 seconds exposure, the surface had cured tack-free.

A similar experiment was carried out with the composition of Example 9. After 60 seconds irradiation, the cured material had a tacky surface.

A similar experiment was carried out with the composition of Example 11. In this case, the surface of the coated slide was found to be tack-free after 10 seconds exposure.

EXAMPLE 13

A light sensitive composition was prepared by blending together the following ingredients:

| | |
|---|---|
| styryloxy resin of Example 3 | 35 g |
| 4-allyloxystyrene of Example 7 | 35 g |
| photocationic catalyst GE 1014 | 2.1 g |

The liquid composition was poured into a thin polyester sheet 15×15 cm$^2$ (MELINEX, I.C.I.) supported by a glass plate. 2 mm spacers were placed around the edges of the supported film and a second polyester sheet brought in contact with the liquid. A second glass plate was placed on top of the top polyester sheet and the liquid compressed to form a 0.2 cm thick sandwich. The top glass plate was removed and the coating exposed to UV light from a Fusions System lamp (20 cm, 80 mWcm$^{-2}$) for 2×20 seconds exposures through the polyester film. The semi-cured sandwich was turned over and the base glass plate removed. The coating was then exposed to UV light for a second period of 2×20 seconds to complete the cure. The polyester films were peeled from the cured resin. Standard "dog-bone" test specimen pieces (0.6 cm width, overall length 11.5 cm and tab width 0.6 cm) were cut from the cured stryloxy sheet and the tensile breaking strength and % elongation measured using standard tensile testing equipment. The results obtained are as follows:

| Test Specimen No. | Cross Sectional area (cm$^2$) | % Elongation | Tensile Strength at Break dN |
|---|---|---|---|
| 1 | 0.159 | 52 | 41.5 |
| 2 | 0.147 | 40 | 28.6 |
| 3 | 0.179 | 54 | 31.3 |

The Shore A hardness of the cured film was measured at 16 different points and the average value obtained was 71 with a range 58–80.

EXAMPLE 14

A solution of 2,2,4-trimethylhexamethylene diisocyanate (10.5 g, 0.05 m) 4-(2′-hydroxyethoxy) styrene (16.4 g, 0.1 m, Example 2) and stannous (II) ethylhexanoate (0.27 g) in chloroform 75 ml was refluxed for 40 minutes. After this time, the characteristic I.R. peak for —NCO group at 2275 cm$^{-1}$ had disappeared indicating the reaction to be completed. The G.P.C. chromatogram indicated about 95% single product higher in molecular weight than either starting material. The solvent was removed under reduced pressure to yield a white solid, which was purified by washing with petrol (b.p. 40°–60° C.) to yield styryloxy urethane resin (25.5 g) of the structure X:

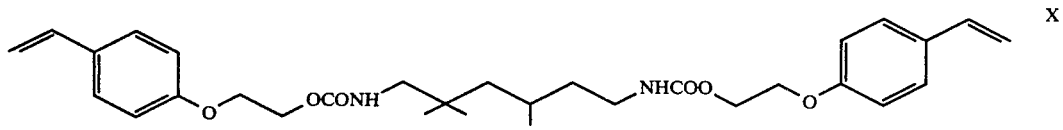

which was confirmed by I.R. spectroscopy (NaCl disc) 3,060, 3,050, 1620, 980 cm$^{-1}$, characteristic absorption bands of unsubstituted styryl group, 3,310, 1690 cm$^{-1}$ characteristic bands of urethane group; 2940, 1600 cm$^{-1}$ characteristic bands of saturated and aromatic hydrocarbon groups respectively.

EXAMPLE 15

Methane sulfonic acid (one drop) was added to styryloxy resin (1 g) of Example 14. The product immediately underwent a solid state polymerization to form a pink coloured solvent-insoluble gel.

EXAMPLE 16

Part A

A solution of isophorone diisocyanate (5.55 g 0.025 m), 4-(2'-hydroxyethoxy) benzaldehyde (8.3 g, 0.05 m, Example 1) and tin (II) ethylhexanoate (0.14 g) in chloroform (25 ml) was refluxed under N$_2$ for 75 minutes after which time the I.R. spectrum of the mixture showed complete consumption of the isocyanate (no peak at 2,240 cm$^{-1}$). The solvent was removed under reduced pressure and the residue taken up in dry tetrahydrofuran (THF) (10 ml).

Part B

In a 100 ml round bottomed flask equipped with a mechanical stirrer, N$_2$ inlet, reflux condenser and dropping funnel, sodium amide (1.3 g of 90% purity, 0.03 m) was dispersed in THF (50 ml). Methyltriphenylphosphonium bromide (10.71 g, 0.03 m) was added and the mixture stirred at room temperature for 2 hours. The solution prepared as described in Part A was added over 5 minutes and the stirred mixture heated under reflux for 4 hours. The contents of the flask were carefully poured onto water (300 mls) and extracted with CH$_2$Cl$_2$ 3×100 mls. The combined extracts were dried (Na$_2$SO$_4$) and the solvent removed to give 15.9 g of a crude product which was shown by G.P.C., N.M.R. and I.R. analysis to contain the di-styryloxy compound of the formula XI:

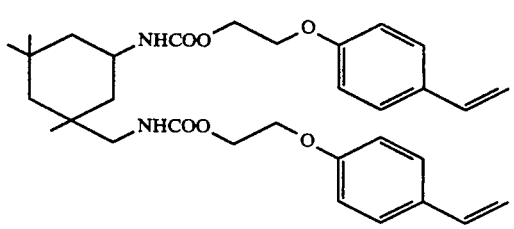

along with quantities of triphenylphosphine oxide and the monostyryloxy compound of the formula XII:

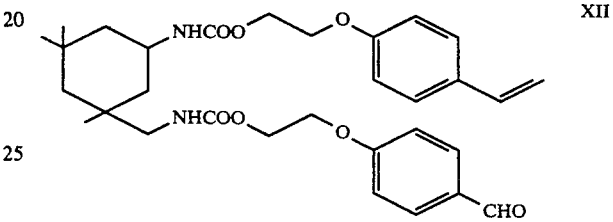

EXAMPLE 17

Methane sulfonic acid (one drop) was added to the resin prepared as described in Example 16 (1 gram). The product immediately turned an intense pink colour characteristic of cationic polymerization.

EXAMPLE 18

A mixture of Varamol 106 (50.08 g) (10% solution of vinyl guaiacol in EtOH supplied by I.F.F. =0.033 moles vinyl guaiacol), allylglycidyl ether (3.47 g, 0.033 m), Amberlyst resin A27 (0.68 g) and benzyltrimethylammonium hydroxide (0.80 g of 40% solution in methanol) was heated under reflux for 65 hours. T.l.c. and G.P.C. analysis indicated complete consumption of starting compounds and G.P.C. showed the product to comprise a mixture of high and low molecular weight fractions. The solvent was removed under reduced pressure and the residue dissolved in CHCl$_3$. The solution was filtered through a short silica column and the solvent removed to yield an orange coloured viscous material (6.8 g). An aliquot (0.09 g) was separated by P.L.C. (50% p. spirit in Et$_2$O) and gave 4-(3'-allyloxy-2'-hydroxypropoxy)-3-methoxystyrene (0.462 g, 40%) along with some minor impurities. $^1$H (NMR (CDCl$_3$): $\tau$3.2, m, 3H, AR—H; $\tau$3.4–4.5 m, 3H, Ar-CH=CH$_2$; $\tau$4.85, m, 3H, allyl— CH=CH$_2$; $\tau$6.2, m, 11H, 3×OCH$_3$. I.R. (NaCl)=3450 cm$^{-1}$, —OH. GPC ($\mu$ styragel, CH$_2$Cl$_2$): two peaks 25.1 and 24.5 ml.

EXAMPLE 19

A solution of 4,-(3'-allyloxy-2'-hydroxypropoxy)-3-methoxy-styrene (5.28 g, 0.02 m, prepared as described in Example 18), isophoronediisocyanate (2.23 g, 0.01 m) and stannous ethyl-hexanoate (0.075 g) in chloroform (30 mls) was heated under reflux in a N$_2$ atmosphere for 1.5 hours. T.l.c. analysis showed the complete consumption of the starting hydroxyl-containing styrene and the formation of a single new product corresponding to the styryloxy urethane of the structure XIII:

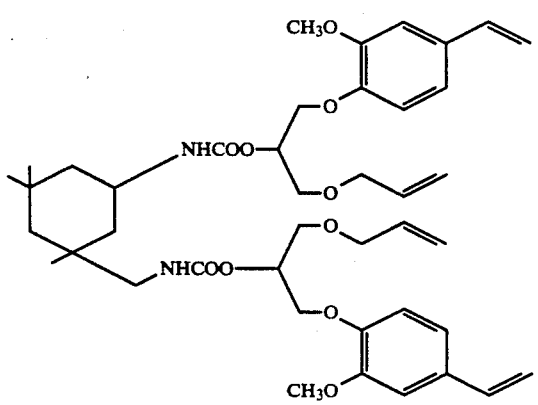

XIII

EXAMPLE 20

Cationically active compositions were prepared by blending together the following compounds in parts by weight:

| Compound | Composition A | Composition B |
|---|---|---|
| Styryloxy-urethane of Example 19 | 55.8 | 70.2 |
| Anisole | 43.0 | 28.1 |
| Benzenediazonium Hexafluorophosphate | 1.2 | 1.7 |

Aliquots (1 g) of each composition were heated at 82° C. for 15 minutes. After this time, both samples had cured to a solvent insoluble purple gel.

We claim:

1. Cationically polymerisable styryloxy resins having urethane linkages, represented by the formula III:

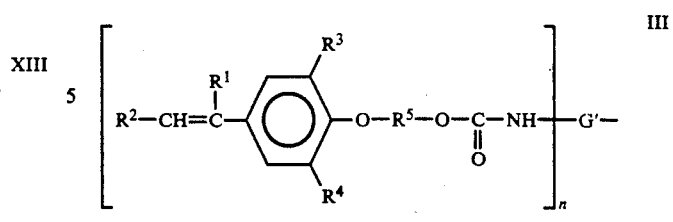

wherein
$R^1$ and $R^2$ are H, or one of $R^1$ and $R^2$ is H and the other is methyl;
$R^2$ and $R^4$, are H, lower alkyl, or alkoxy if $R^2$ is not methyl;
$R^5$ is a divalent hydrocarbon radical;
$G^1$ is the residue of an n-valent isocyanate propolymer prepared by reaction of hydroxyl terminated hydrocarbon polymer halohydrocarbon selected from the goups consisting of a diene homopolymers and copolymers with an aromatic or aliphatic diisocyanate, said prepolymer being free of amino, aliphatic thiol, aliphatic hydroxyl or other groups which interfere with cationic polymerisation;
and n is an integer of 2 or more.

2. Resins according to claim 1 wherein the diene homopolymer or copolymer has a number average molecular weight in the range from about 400 to about 25,000.

3. Resins according to claim 1 wherein the hydroxyl terminated hydrocarbon or halohydrocarbon polymer is a hydroxyl-terminated polymer or copolymer of a diene having up to 12 carbon atoms, optionally substituted with one or more lower alkyl, aryl or halogen groups.

4. Resins according to claim 3 wherein the diene is selected from buta-1,3-diene, 2-methyl-buta-1,3-diene (isoprene), 2-chlorobuta-1,3-diene (chloroprene), 2,3-dimethyl-buta-1,3-diene, and buta-1,2-diene.

5. Resins according to claim 1 wherein $R^3$ is H, methyl, or methoxy and $R^4$ is H.

6. Resins according to claim 1 wherein $R^5$ is a saturated or unsaturated linear hydrocarbon having up to about 5 carbon atoms or a cycloaliphatic or aromatic hydrocarbon having up to about 10 carbon atoms.

7. A resin as in claim 4 wherein said hydroxyl terminated polymer is a copolymer of said diene and styrene.

8. A resin as in claim 2 wherein said molecular weight is in the range of from 1,000 to 5,000.

9. A resin according to claim 3 wherein said diene is a diene having up to 6 carbon atoms.

* * * * *

UNITED STATES PATENT AND TRADEMARK OFFICE
CERTIFICATE OF CORRECTION

PATENT NO. : 5,019,629

DATED : May 28, 1991

INVENTOR(S) : John Woods et al

It is certified that error appears in the above-identified patent and that said Letters Patent is hereby corrected as shown below:

Col. 14, line 17, delete "propo-" and insert -- prepo- --

Col. 14, line 20, delete "goups" and insert -- groups --

Signed and Sealed this

Third Day of March, 1992

Attest:

HARRY F. MANBECK, JR.

*Attesting Officer*  *Commissioner of Patents and Trademarks*